US012010963B2

(12) United States Patent
Zhou et al.

(10) Patent No.: US 12,010,963 B2
(45) Date of Patent: Jun. 18, 2024

(54) MEDIUM AND CULTURE METHOD FOR BLUEBERRY TISSUE CULTURE

(71) Applicant: SHANDONG DAFENGYUAN AGRICULTURE CO., LTD., Rizhao (CN)

(72) Inventors: Yangyan Zhou, Rizhao (CN); Weijian Sun, Rizhao (CN); Wenxiu Chen, Rizhao (CN); Aowei Mo, Rizhao (CN); Peng Guo, Rizhao (CN); Penghao Xu, Rizhao (CN)

(73) Assignee: Shandong Dafengyuan Agriculture Co., Ltd., Rizhao (CN)

( * ) Notice: Subject to any disclaimer, the term of this patent is extended or adjusted under 35 U.S.C. 154(b) by 0 days.

(21) Appl. No.: 17/720,652

(22) Filed: Apr. 14, 2022

(65) Prior Publication Data

US 2022/0338435 A1    Oct. 27, 2022

(30) Foreign Application Priority Data

Apr. 16, 2021    (CN) .......................... 202110414403.0

(51) Int. Cl.
*A01H 6/36*    (2018.01)
*A01G 22/05*    (2018.01)
(Continued)

(52) U.S. Cl.
CPC .............. *A01H 4/002* (2021.01); *A01G 22/05* (2018.02); *A01G 24/15* (2018.02); *A01G 24/22* (2018.02); *A01H 4/001* (2013.01); *A01H 5/08* (2013.01); *A01H 6/368* (2018.05); *C12N 5/0025* (2013.01); *C12N 5/04* (2013.01); *C12N 2500/05* (2013.01); *C12N 2500/32* (2013.01);
(Continued)

(58) Field of Classification Search
CPC .......... A01H 4/00; A01H 4/002; A01H 4/005; A01H 4/001; C12N 5/04; C12N 5/0025; A01G 22/05; A01G 24/15; A01G 24/22
See application file for complete search history.

(56) References Cited

FOREIGN PATENT DOCUMENTS

CN    101176428 A    5/2008
CN    105028193 A    11/2015
(Continued)

OTHER PUBLICATIONS

Qiu et al.; Regeneration of Blueberry Cultivars through Indirect Shoot Organogenesis; HortScience 53(7); 1045-1049; 2018.*

*Primary Examiner* — Kent L Bell
(74) *Attorney, Agent, or Firm* — United IP Counselors, LLC

(57) ABSTRACT

The invention provides a callus induction medium for blueberry tissue culture, taking woody plant medium (WPM) as a basic medium, and including: 0.5-5.0 mg/L forchlorfenuron (CPPU) and 0.1-0.4 mg/L 2-isopentenyladenine (2-ip). The present invention also provides a callus culture method for blueberry, including inoculating the blueberry explant into the above callus induction medium to conduct induction culture in order to form blueberry callus. The present invention also discloses the medium combination and culture method to culture the above blueberry callus to blueberry tissue culture plant. For the above medium and culture method, the differentiation effect is good, efficiency is high, one can conduct continuous differentiation, and the effect is better on multiple varieties.

6 Claims, 3 Drawing Sheets

(51) Int. Cl.
*A01G 24/15* (2018.01)
*A01G 24/22* (2018.01)
*A01H 4/00* (2006.01)
*A01H 5/08* (2018.01)
*C12N 5/00* (2006.01)
*C12N 5/04* (2006.01)

(52) U.S. Cl.
CPC ...... *C12N 2500/34* (2013.01); *C12N 2500/35* (2013.01); *C12N 2500/38* (2013.01); *C12N 2500/60* (2013.01); *C12N 2501/30* (2013.01); *C12N 2533/76* (2013.01)

(56) References Cited

FOREIGN PATENT DOCUMENTS

| | | | |
|---|---|---|---|
| CN | 105087637 | A | 11/2015 |
| CN | 106613939 | A | 5/2017 |
| CN | 106982737 | A | 7/2017 |
| CN | 109984043 | A | 7/2019 |
| KR | 20130117297 | A | 10/2013 |

* cited by examiner

MEDIUM AND CULTURE METHOD FOR BLUEBERRY TISSUE CULTURE

BACKGROUND

Field of Invention

The present invention belongs to the field of plant tissue culture, relates to a medium and a culture method for blueberry tissue culture, and particularly relates to a medium and a culture method for blueberry leaves callus inducing and budding and obtaining blueberry tissue culture plant.

Background of the Invention

Blueberry (*Vaccinium* SPP) is a perennial low shrub of *vaccinum, ericaceae*, which is native to North America and East Asia, distributed in North Korea, Mongolia, Europe, North America and areas of Heilongjiang, Inner Mongolia, Jilin, Changbaishan and the like in China. The blueberry fruit is rich in nutrients and anthocyanin, and has function of preventing brain nerve aging, strong heart, anti-cancer, softening blood vessels, and enhancing human immunity and the like. Because of its superior healthcare value, it is popular in the world and one of the five healthy fruits recommended by the World Food and Agriculture Organization.

The Chinese patent application under application No. 200710157193.1 discloses a medium composition for the proliferation of blueberry test tube seedlings and the method thereof, but the callus induction of the method is low and cannot fully meet the demand for blueberry tissue culture.

SUMMARY OF THE INVENTION

In order to solve problems that exist in the prior art, the first aspect of the present invention provides a callus induction medium for blueberry tissue culture, the callus induction medium takes woody plant medium (WPM) as basic medium, the basic medium comprises: 0.5-5.0 mg/L (for example, 0.6 mg/L, 0.8 mg/L, 1.0 mg/L, 1.2 mg/L, 1.4 mg/L, 1.6 mg/L, 1.8 mg/L, 2.0 mg/L, 2.2 mg/L, 2.4 mg/L, 2.6 mg/L, 2.8 mg/L, 3.0 mg/L, 3.2 mg/L, 3.4 mg/L, 3.6 mg/L, 3.8 mg/L, 4.0 mg/L, 4.2 mg/L, 4.4 mg/L, 4.6 mg/L, 4.8 mg/L) CPPU forchlorfenuron (CPPU) and 0.1-0.4 mg/L (for example, 0.12 mg/L, 0.14 mg/L, 0.16 mg/L, 0.18 mg/L, 0.20 mg/L, 0.22 mg/L, 0.24 mg/L, 0.26 mg/L, 0.28 mg/L, 0.30 mg/L, 0.32 mg/L, 0.34 mg/L, 0.36 mg/L, 0.38 mg/L) 2-isopentenyladenine (2-ip).

In some embodiments, the variety of the blueberry is selected from JE, Duke, Bluecrop and Sweetheart.

In some embodiments, the callus induction medium comprises: 2.0-4.0 mg/L CPPU and 0.2-0.3 mg/L 2-ip.

In some embodiments, the callus induction medium comprises: 2.0 mg/L CPPU and 0.2 mg/L 2-ip.

In some embodiments, the WPM medium comprises: 4-8 g/L agar and 20-30 g/L sucrose.

In some embodiments, the WPM medium further comprises: 400 mg/L Ammonium Nitrate, 370 mg/L Magnesium Sulfate Heptahydrate, 278 mg/L Calcium Nitrate Tetrahydrate, 200 mg/L Potassium Nitrate, 170 mg/L Potassium Dihydrogen Phosphate, 8.6 mg/L Zinc Sulfate Heptahydrate, 22.4 mg/L Manganese Sulfate Monohydrate, 0.25 mg/L Sodium Molybdate Dihydrate, 0.25 mg/L Copper Sulfate Pentahydrate, 73.4 mg/L Sodium Iron Ethylene Diamine Tetracetate, 100 mg/L Inositol, 2 mg/L Glycine, 0.5 mg/L Thiamine Hydrochloride, 0.5 mg/L Niacin and 0.1 mg/L Pyridoxine Hydrochloride.

In some embodiments, the pH of the callus induction medium falls in a range of 5.0-5.5.

The second aspect of the present invention provides a medium combination for blueberry tissue culture, the medium combination comprises the callus induction medium of the first aspect of the present invention, a bud growth medium and a rooting medium.

In some embodiments, the bud growth medium takes WPM medium as basic medium, and the bud growth medium comprises: 0.5-1.5 mg/L CPPU (for example, 0.6 mg/L, 0.7 mg/L, 0.8 mg/L, 0.9 mg/L, 1.0 mg/L, 1.2 mg/L, 1.3 mg/L, 1.4 mg/L) and 0.2-0.6 mg/L (for example, 0.25 mg/L, 0.3 mg/L, 0.35 Mg/L, 0.4 mg/L, 0.45 mg/L, 0.5 mg/L, 0.55 mg/L) 2-ip.

In some embodiments, the bud growth medium comprises: 0.8-1.2 mg/L CPPU and 0.3-0.5 mg/L 2-ip.

In some embodiments, the bud growth medium comprises: 1.0 mg/L CPPU and 0.4 mg/L 2-ip.

In some embodiments, the pH of the bud growth medium falls in a range of 5.0-5.5.

In some embodiments, the rooting medium takes 1/2 MS Murashige and Skoog (MS) medium as basic medium, the rooting medium comprises: 0.2-4.0 mg/L (for example, 0.5 mg/L, 1.0 mg/L, 1.5 mg/L, 2.0 mg/L, 2.5 mg/L, 3.0 mg/L, 3.5 mg/L) naphthyl acetic acid (NAA).

In some embodiments, the rooting medium comprises: 1.0-3.0 mg/L NAA.

In some embodiments, the rooting medium comprises: 2.0 mg/L NAA.

In some embodiments, the pH of the rooting medium falls in a range of 5.0-5.5.

In some embodiments, the medium combination further comprises callus subculture medium.

In some embodiments, the callus subculture medium takes WPM medium as basic medium, and the callus subculture medium comprises: 0.3-5.0 mg/L CPPU (for example, 0.5 mg/L, 1.0 mg/L, 1.5 mg/L, 2.0 mg/L, 2.5 mg/L, 3.0 mg/L, 3.5 mg/L, 4.0 mg/L, 4.5 mg/L).

In some embodiments, the callus subculture medium comprises: 2.0-4.0 mg/L CPPU.

In some embodiments, the callus subculture medium comprises: 3.0 mg/L CPPU.

In some embodiments, the pH of the callus subculture medium falls in a range of 5.0-5.5.

In some embodiments, the WPM medium comprises: 4-8 g/L of agar and 20-30 g/L of sucrose.

In some embodiments, the WPM medium further comprises: 400 mg/L Ammonium Nitrate, 370 mg/L Magnesium Sulfate Heptahydrate, 278 mg/L Calcium Nitrate Tetrahydrate, 200 mg/L Potassium Nitrate, 170 mg/L Potassium Dihydrogen Phosphate, 8.6 mg/L Zinc Sulfate Heptahydrate, 22.4 mg/L Manganese Sulfate Monohydrate, 0.25 mg/L Sodium Molybdate Dihydrate, 0.25 mg/L Copper Sulfate Pentahydrate, 73.4 mg/L Sodium Iron Ethylene Diamine Tetracetate, 100 mg/L Inositol, 2 mg/L Glycine, 0.5 mg/L Thiamine Hydrochloride, 0.5 mg/L Niacin and 0.1 mg/L Pyridoxine Hydrochloride.

In some embodiments, the 1/2 MS medium comprises: 5-9 g/L agar and 15-25 g/L sucrose.

In some embodiments, the 1/2 MS medium further comprises: 950 mg/L Potassium Nitrate, 166.1 mg/L Calcium Chloride, 825 mg/L Ammonium Nitrate, 90.35 mg/L Magnesium Sulfate, 85 mg/L Potassium Dihydrogen Phosphate, 0.025 mg/L Copper Sulphate, 6.2 mg/L Boric Acid, 16.9 mg/L Manganese Sulfate, 0.25 mg/L Sodium Molybdate, 8.6 mg/L Zinc Sulfate, 0.025 mg/L Cobalt Chloride, 0.83 mg/L Potassium Iodide, 27.8 mg/L FeSO$_4$·7H$_2$O, 37.26 mg/L Na$_2$-EDTA·2H$_2$O, 2.0 mg/L Glycine, 100 mg/L Inositol, 0.50 mg/L Niacin, 0.1 mg/L Thiamine Hydrochloride and 0.5 mg/L Pyridoxine Hydrochloride.

The third aspect of the present invention provides a callus culture method of blueberry,
    inoculating the blueberry explant into the callus induction medium of the first aspect of the present invention to conduct induction culture, to form blueberry callus.

In some embodiments, the induction culture is dark culture.

In some embodiments, in the induction culture, the temperature falls in a range of 22-26° C.

In some embodiments, in the induction culture, time falls in a range of 12-22 days.

In some embodiments, the blueberry explant is a sterile blueberry leaf.

In some embodiments, the sterile blueberry leaf is cut and then inoculated.

In some embodiments, the abaxial surface of the sterile blueberry leaf is adjacent to the callus induction medium for inoculating.

In some embodiments, the sterile blueberry leaf is taken from the blueberry tissue culture seedlings.

The fourth aspect of the present invention provides a blueberry tissue expansion propagation method, conducting bud growth culture and rooting culture sequentially to the blueberry callus cultured by the callus culture method of the third aspect of the present invention, to obtain a blueberry tissue culture plant.

In some embodiments, inoculating the callus lumps of the blueberry callus into the bud growth medium of the medium combination of the second aspect of the present invention to conduct bud growth culture, to form the blueberry plant growing adventitious buds.

In some embodiments, in the bud growth culture, the temperature falls in a range of 22-26° C.

In some embodiments, in the bud growth culture, the light time falls in a range of 14-18 hours a day.

In some embodiments, in the bud growth culture, the light intensity falls in a range of 1500-3000 lx.

In some embodiments, in the bud growth culture, the culture time falls in a range of 12-22 days.

In some embodiments, inoculating the blueberry plant growing adventitious buds into the rooting medium of the medium combination of the second aspect of the present invention to conduct rooting culture, to form the blueberry plant growing adventitious buds and root.

In some embodiments, in the rooting culture, the temperature falls in a range of 22-26° C.

In some embodiments, in the rooting culture, the light time falls in a range of 14-18 hours a day.

In some embodiments, in the rooting culture, the light intensity falls in a range of 1500-3000 lx.

In some embodiments, in the rooting culture, the culture time falls in a range of 15-35 days.

In some embodiments, the tissue expansion propagation method also includes callus subculture, the step thereof comprises:
    inoculating the blueberry callus into the callus subculture medium of the medium combination of the second aspect of the invention to conduct callus subculture.

In some embodiments, the subculture is dark culture.

In some embodiments, in the subculture, the temperature falls in a range of 22-26° C.

In some embodiments, in the subculture, the time falls in a range of 20-30 days.

In some embodiments, the tissue expansion propagation method also comprises: conducting seedling hardening and transplanting to the blueberry plant growing adventitious buds and root, to obtain blueberry cultivated plant.

In some embodiments, the step of the seedling hardening comprises: maintaining the humidity of the inside of the culture bottle having the blueberry plant growing adventitious buds and root to be 65-75% for 0.5-1.5 days, then maintaining the humidity of 55-65% for 5-9 days under ventilation conditions.

In some embodiments, in the step of the seedling hardening, the lighting time falls in a range of 14-18 hours a day.

In some embodiments, in the step of the seedling hardening, the light intensity falls in a range of 1500-3000 lx.

In some embodiments, cleaning and removing the medium from the blueberry plant growing adventitious buds and root after seedling hardening, to conduct the transplanting.

In some embodiments, the culture soil for transplanting is vermiculite: nutritious soil: moss in mass ratio of 1:0.5-1.5: 0.5-1.

The techniques of the present invention are beneficial to prior art:

Using the callus induction medium of blueberry leaves of the present invention to improve the reproduction efficiency of blueberry, and the continuous differentiation ability for the induced callus is strong. Inducing blueberry leaves to produce callus and re-differentiation, differentiation effect is good, efficiency is high, and can conduct continuous differentiation, and the effect to multiple varieties are all better.

DETAILED DESCRIPTION OF THE EMBODYMENTS

Figure 1:
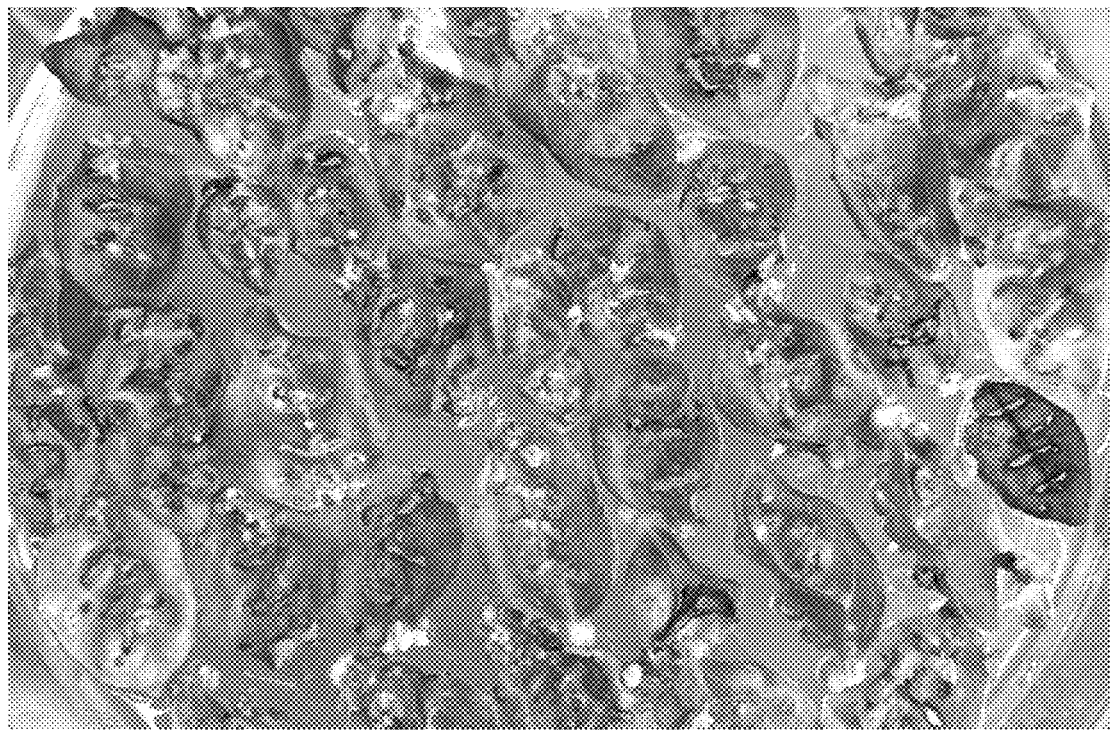
FIG. 1 is a photo of the callus induction and differentiation of JE leaf.

In order to make the purpose, technical solutions and advantages of the present invention more clear, the embodiments of the present invention will be further described in details in combination with Figures bellow.

In the present invention, all the steps not described in details are conventional operations in the art, and all materials not recorded in details are conventional materials in the art.

EXAMPLE 1

Tissue Culture of JE Variety Blueberry (One) Preparation of Mediums (1) Callus Induction Medium All #1 to #18 callus induction medium of the present invention take WPM medium as basic medium, and WPM basic medium contains 25 g/L sucrose, 6.5 g/L agar, pH is 5.2, other conventional ingredients in formulation are shown in table 1 and the hormone ingredients are shown in column 2 of Table 2.

TABLE 1

Other ingredients in the WPM medium formulation

| Classification | Ingredient | Content mg/L |
|---|---|---|
| Macroelement | Ammonium Nitrate, $NH_4NO_3$ | 400 |
| | Magnesium Sulfate Heptahydrate, $MgSO_4 \cdot 7H_2O$ | 370 |
| | Calcium Nitrate Tetrahydrate, $Ca(NO_3)_2 \cdot 4H_2O$ | 278 |
| | Potassium Nitrate, $KNO_3$ | 200 |
| | Potassium Dihydrogen Phosphate, $KH_2PO_4$ | 170 |
| Microelement | Zinc Sulfate Heptahydrate, $ZnSO_4 \cdot 7H_2O$ | 8.6 |
| | Manganese Sulfate Monohydrate, $MnSO_4 \cdot H_2O$ | 22.4 |
| | Sodium Molybdate Dihydrate, $NaMo_4 \cdot 2H_2O$ | 0.25 |
| | Copper Sulfate Pentahydrate, $CuSO_4 \cdot 5H_2O$ | 0.25 |
| Ferric Salts | Sodium Iron Ethylene Diamine Tetracetate | 73.4 |
| Organics | Inositol | 100 |
| | Glycine | 2 |
| | Thiamine Hydrochloride | 0.5 |
| | Niacin | 0.5 |
| | Pyridoxine Hydrochloride | 0.1 |

(2) Callus Subculture Medium

Taking WPM medium as basic medium (see Table 1 for the formulation), WPM basic medium contains 25 g/L sucrose, 6.5 g/L agar, pH is 5.2, hormone is CPPU, see column 2 of Table 3 for hormone content.

(3) Bud Growth Medium

Taking WPM medium as basic medium (see Table 1 for the formulation), WPM basic medium contains 25 g/L sucrose, 6.5 g/L agar, pH 5.2, hormones are CPPU and 2-ip, see columns 2-3 of Table 4 for hormone content.

(4) Rooting Medium

Taking 1/2MS medium as basic medium, 1/2MS basic medium contains 20 g/L sucrose, 7 g/L agar, pH falls in a range of 5.2-5.4, hormone is NAA, see columns 2 of Table 5 for the hormone content.

1/2MS medium specific further comprises macroelement such as 950 mg/L Potassium Nitrate, 166.1 mg/L Calcium Chloride, 825 mg/L Ammonium Nitrate, 90.35 mg/L Magnesium Sulfate, 85 mg/L of Potassium Dihydrogen Phosphate; microelement such as 0.025 Mg/L Copper Sulphate, 6.2 mg/L Boric Acid, 16.9 mg/L Manganese Sulfate, 0.25 mg/L Sodium Molybdate, 8.6 mg/L Zinc Sulfate, 0.025 mg/L Cobalt Chloride, 0.83 mg/L Potassium Iodide; ferric salts such as 27.8 mg/L $FeSO_4 \cdot 7H_2O$, 37.26 mg/L $Na_2$-$EDTA \cdot 2H_2O$; organics such as 2.0 mg/L Glycine, 100 mg/L Inositol, 0.50 mg/L Niacin, 0.1 mg/L Thiamine Hydrochloride(VB1), 0.5 mg/L Pyridoxine Hydrochloride (VB6).

(Two) Acquisition and Treatment of Blueberry Leaf Explant

Choosing a robust blueberry sterile tissue culture seedling grown for 2-4 weeks, using sterilized tissue culture scissors cut the upper stein, on the sterilized filter paper board, using sterilized scalpel to cut the young leaf and cutoff petiole, and put the leaf into the medium plate without any nutrient ingredient (i.e., only 7 g/L agar, pH falls in a range of 5.2-5.3) for use.

In this step, using blueberry sterile tissue culture seedling is for saving the step of explant disinfection treatment, to improve efficiency, increase the sterile effect, and promote the continuity of production. The present invention can also use robust and young blueberry leaves, and obtain sterile blueberry leaves by conventional disinfection for the subsequent operations.

(Three) Callus Induction and Budding (1) putting front surface (i.e., adaxial surface) of leaves upwardly, cutting them 2-3 times obliquely in the direction perpendicular to the main leaf veins, pay attention not to cut the leaves into pieces, cut once, do not cut back and forth; using pointed tweezers to prick on leaves 3-4 times to better promote the induction of callus; replace a sterile filter paper after cutting each 10 leaves.

(2) putting front surface of leaves upwardly, tile them onto the medium in the culture dish, and make the back surface of the leaves contact the medium sufficiently, leaving a gap of 0.5 cm among the leaves to give the leaves sufficient growth space.

(3) Sealing the culture dish, placing the culture dish upright at 24° C. in dark culture room, dark culturing for 15-20 days.

(4) Taking the culture dish from the dark culture room, placing it at 24° C., culturing it in a 16 h illumination/8 hour dark environment each day for 15-30 days, the light intensity falls in a range of 1500-3000 lx, to induce the differentiation of the bud.

Using the blueberry explant of the JE variety, respectively adopting the callus induction mediums containing the 18 kinds of hormone combinations shown in Table 2, the number of culture dish per medium was 10. Observing the callus induction condition and growth, callus time, the state of callus, the color of callus, callus induction rate (only calculating living leaves) and callus differentiation rate of the explant (i.e., leaf tissue), wherein, the callus differentiation rate is calculated after the light culture of step (4), and other indicators are calculated after dark culture of step (3), see Table 2 for the results respectively.

It can be seen from the data of Table 2, and the effect of #8 callus induction medium is best, wherein see FIG. 1 for one medium board after light culture of step (4).

Using stereomicroscope(manufacturer is leica, model is M205C) to observe the blueberry leaf with callus cultured by #8 callus induction medium of step (4), the magnification was 6.3 times, observing the callus and buds. See FIG. 2 for the photos of a series of views.

Figure 2:
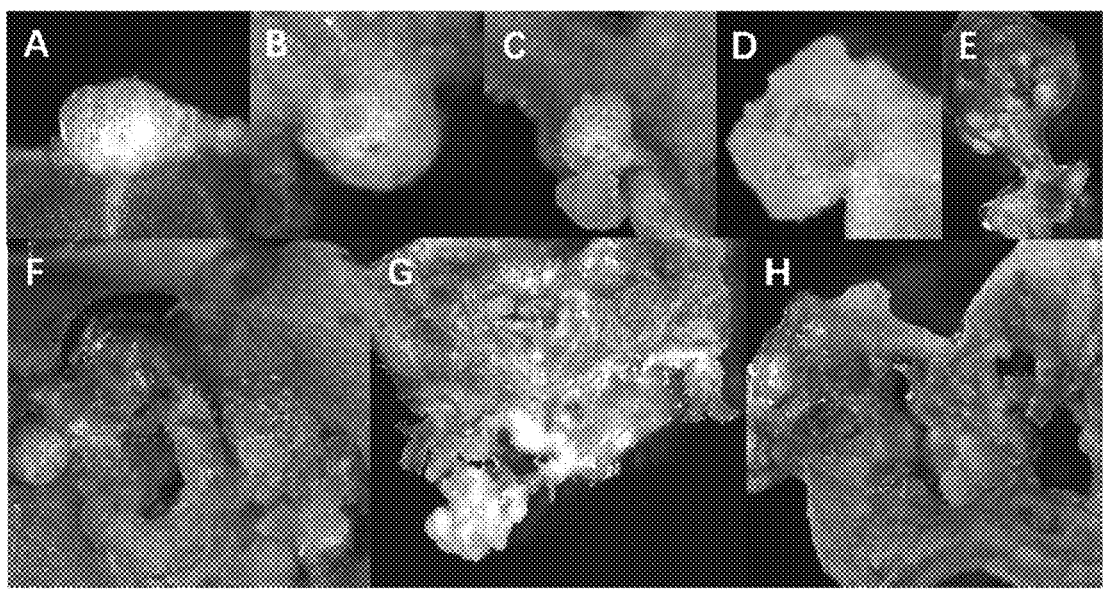
FIG. 2 is a photo of the callus induced from JE leaf and the buds differentiated there from under the stereomicroscope.

It can be seen according to Table 2 and FIG. 1-2, using the combination of CPPU (forchlorfenuron) and 2-ip(2-isopentene adenine) as hormone, the indexes of callus induction rate and the callus differentiation rate are obviously better, of which #8callus induction medium is best, and it can effectively induce blueberry explant to generate callus.

The process that the callus differentiates into the bud (A-F) can be clearly seen in FIG. 2, they are respectively the emergence of bud primordium(A), the growth of bud primordium (B-D), the appearance of the bud (E), and the bud visible to the naked eyes (F-H), cut the buds off in H, each can grow into a complete blueberry tissue culture seedling.

(Four) Callus Subculturing:

Filter out the callus growing well, growing strong, without differentiation and budding cultured in the best medium (#8 callus medium) after the dark culture of step (3) in step (three), placing it into the sterile ultra-clean workbench, the subsequent operations needs the sterile operation to be operated in sterile ultra-clean workbench.

Using sterile scalpel to cut the selected callus into pieces in size of length and width (0.5×0.5) cm, planting them into subculture medium of blueberry callus containing the hormone of 5 concentrations shown in table 3 to process subculture and proliferative culture, 10 plates per medium, and the number of callus in each plate is 10.

Subculturing the above callus in dark chambers for 3-4 weeks, and the culture temperature is 24° C., and observing the proliferation state of callus. See Table 3 for the multiplication coefficient.

It can be seen that the method of this step can effectively subculture the callus.

(Five) Bud Growth Culture

Figure 3:
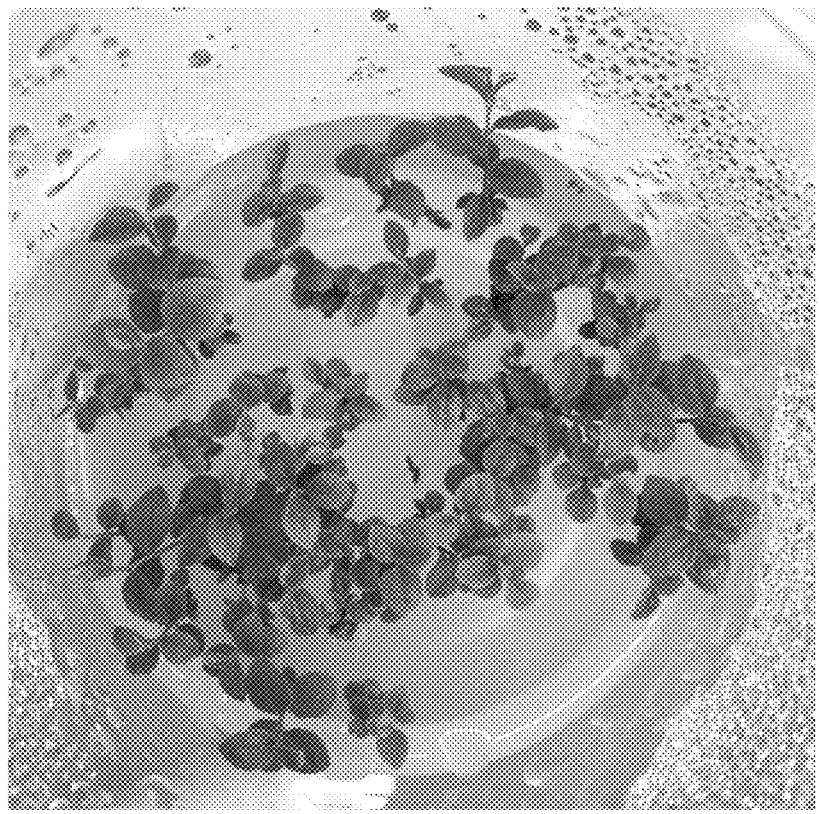
FIG. 3 is a photo shows that a blueberry callus lumps grows to the blueberry tissue culture seedling.

Filter out the callus growing well, growing strong, without differentiation and budding cultured in the best medium (#8 callus medium) after the dark culture of step (3) in step (three)and transplanting them into the Bud growth medium of the four hormone combinations shown in table 4,20-25 plants per bottle, the culture environment is 24° C., culturing for 15-20 days, 16 hours illumination/8 hours darkness per day, light intensity falls in a range of 1500-3000 lx, observing grow status of small seedlings and make records. See FIG. 3 for the photo of one bottle, and see Table 4 for the growth situation.

(Six) Rooting Induction

Figure 4:
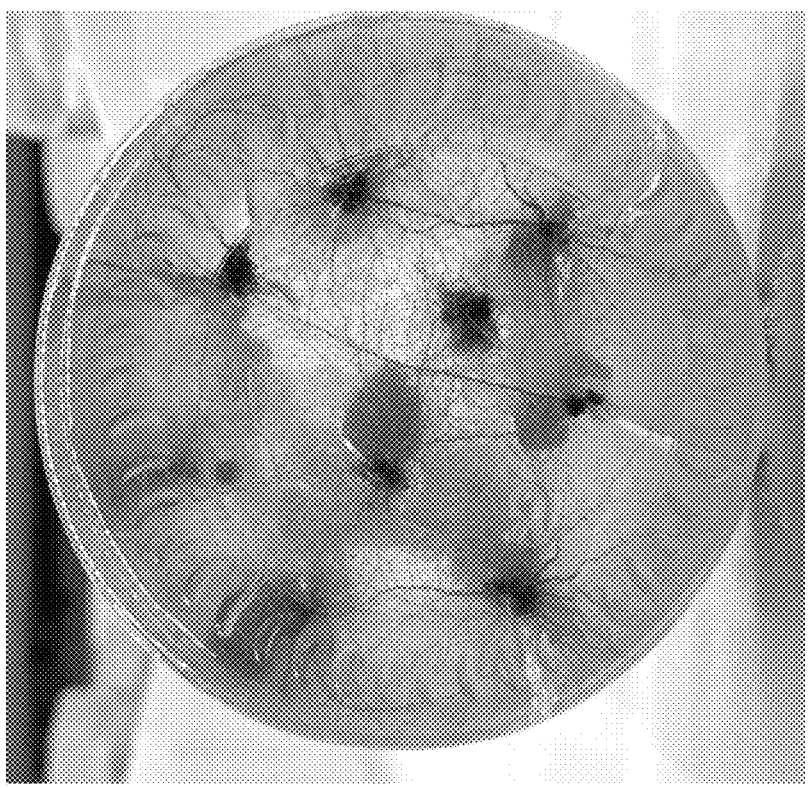
FIG. 4 is a photo of blueberry rooting.

After cutting the strong blueberry seedlings in step (5), transplanting them into the 4 blueberry rooting mediums shown in Tables 1 and 5, and 8-10 plants per bottle, the culture environment was 24° C., 16 hours illumination/8 hours darkness per day, culturing for 20-30 days, light intensity falls in a range of 1500-3000 lx, observing rooting status of small seedlings and recording rooting rate. See FIG. 4 for the photo of one bottle, and see Table 5 for the rooting rate.

(Seven) Seedling Hardening

Conducting seedling hardening to the blueberry plant growing adventitious buds and root, the step of seedling hardening comprises: preparing the blueberry tissue culture seedlings that have been rooted in the aforementioned step (six), open the bottle cap of tissue culture bottle, adding 15 ml sterile water therein, placing it in an environment where humidity is 70%, 1 day later, pouring off the water in the tissue culture bottle, and re-adding 20 ml of sterile water, adjusting the humidity to 60% and performing the ventilation, transplanting 7 days later, the sterile water can be replaced once during the period. The above optical dark cycle is 16 hours illumination/8 hours darkness per day, light intensity falls in a range of 1500-3000 lx.

(Eight) Transplanting

Taking out the blueberry plants after seedling hardening in above step (seven) from the bottle, removing the medium, using water to wash the root, sowing the plant into nutrition pot. The culture soil for transplanting is vermiculite: nutritious soil: moss (1:1:1 in mass ratio), pay attention to control the pH of nutrient soil to fall in a range of 5.3-5.6.

RESULTS: When the conditions are optimized, the final callus induction can reach 97%, and the bud rate of callus (after light culture in step (4)) can reach 71%, and the rooting rate can reach 90%, seedling survival rate (referring to the survival rate of the transplanting stage) can reach 94%.

TABLE 2

Statistics of hormone combination in callus induction medium and their culture effects

| serial number | The combination of different hormones | Time of callus | State of callus | Color of callus | Callus induction rate (only calculating living leaves) | Callus differentiation rate |
|---|---|---|---|---|---|---|
| 1 | 0.5 mg/L CPPU + 0.1 mg/L 2-ip | About 7 d | Compact, present small globular | White | 44% | 19% |
| 2 | 0.5 mg/L CPPU + 0.2 mg/L 2-ip | 7-9 d | Compact | White or light green | 67% | 17% |
| 3 | 0.5 mg/L CPPU + 0.3 mg/L 2-ip | 6-10 d | Compact, the surface small particles are apparent | Light green | 55% | 10% |
| 4 | 1 mg/L CPPU + 0.1 mg/L 2-ip | About 7 d | Compact, globular | White | 66% | 38% |
| 5 | 1 mg/L CPPU + 0.2 mg/L 2-ip | About 7 d | Compact, globular | White | 72% | 35% |
| 6 | 1 mg/L CPPU + 0.3 mg/L 2-ip | About 7 d | Compact, globular, small particles | Light green | 72% | 29% |
| 7 | 2 mg/L CPPU + 0.1 mg/L 2-ip | 5-9 d | Compact, globular | Light yellow | 91% | 66% |

TABLE 2-continued

Statistics of hormone combination in callus induction medium and their culture effects

| serial number | The combination of different hormones | Time of callus | State of callus | Color of callus | Callus induction rate (only calculating living leaves) | Callus different iation rate |
|---|---|---|---|---|---|---|
| 8 | 2 mg/L CPPU + 0.2 mg/L 2-ip | 5-9 d | Compact, presents globular surface small particles are less | White or light yellow | 97% | 71% |
| 9 | 2 mg/L CPPU + 0.3 mg/L 2-ip | 5-9 d | Compact, globular | White or light green | 97% | 54% |
| 10 | 3 mg/L CPPU + 0.1 mg/L 2-ip | 5-9 d | Compact, globular | White | 95% | 49% |
| 11 | 3 mg/L CPPU + 0.2 mg/L 2-ip | 5-9 d | Compact, presents globular, surface small particles are less | White or light green | 93% | 52% |
| 12 | 3 mg/L CPPU + 0.3 mg/L 2-ip | 5-9 d | Compact, globular | White or light green | 98% | 44% |
| 13 | 4 mg/L CPPU + 0.1 mg/L 2-ip | 5-9 d | Compact, globular | White or light yellow | 93% | 36% |
| 14 | 4 mg/L CPPU + 0.2 mg/L 2-ip | 5-9 d | Compact, presents globular, surface small particles are less | White or light yellow | 95% | 27% |
| 15 | 4 mg/L CPPU + 0.3 mg/L 2-ip | 5-9 d | Compact, globular | White or light yellow | 96% | 21% |
| 16 | 0.5 mg/L TDZ + 0.5 mg/L IBA | 8-10 d | Compact, slightly transparent | White or light yellow | 74% | 15% |
| 17 | 0.5 mg/L TDZ + 0.5 mg/L IAA | 8-10 d | Compact, slightly transparent, haying particle | White or light yellow | 82% | 23% |
| 18 | 0.5 mg/L TDZ + 0.5 mg/L NAA | About 10 d | Small particle | white | 5% | 0% |

TABLE 3

Statistics of hormones in blueberry callus subculture medium and their culture effects

| Serial number | CPPU (mg/L) | Multiplication coefficient |
|---|---|---|
| 1 | 0.5 | 0.9 |
| 2 | 1.0 | 1.4 |
| 3 | 2.0 | 1.8 |
| 4 | 3.0 | 2.4 |
| 5 | 4.0 | 1.6 |

TABLE 4

Statistics of hormone combination in blueberry bud growth medium and their culture effects

| Serial number | CPPU (mg/L) | 2-ip (mg/L) | Condition of bud growth |
|---|---|---|---|
| 1 | 0.5 | 0.4 | + |
| 2 | 0.5 | 0.6 | ++ |
| 3 | 1.0 | 0.4 | ++++ |
| 4 | 1.0 | 0.6 | ++ |

Note:
"+" indicates the growth state of the callus.
"++++" indicates the best in growing state, robust growth, fast growing, leaves are large;
"++" indicates that the growth status is common, the growth is slow, and the growth is moderate;
"+" indicates poor growth, slow growth, leaves are small.

TABLE 5

Statistics of the blueberry rooting medium and the culture effect

| Serial number | NAA (mg/L) | Rooting rate (%) | Growth state |
|---|---|---|---|
| 1 | 0.5 | 69% | Rooting is slow |
| 2 | 1.0 | 76% | Adventitious root is more |
| 3 | 2.0 | 90% | Rooting time is short, adventitious root is more |
| 4 | 3.0 | 85% | Rooting time is short, adventitious root is more |

EXAMPLE 2

Tissue Culture of Duke Variety Blueberry

Figure 5:
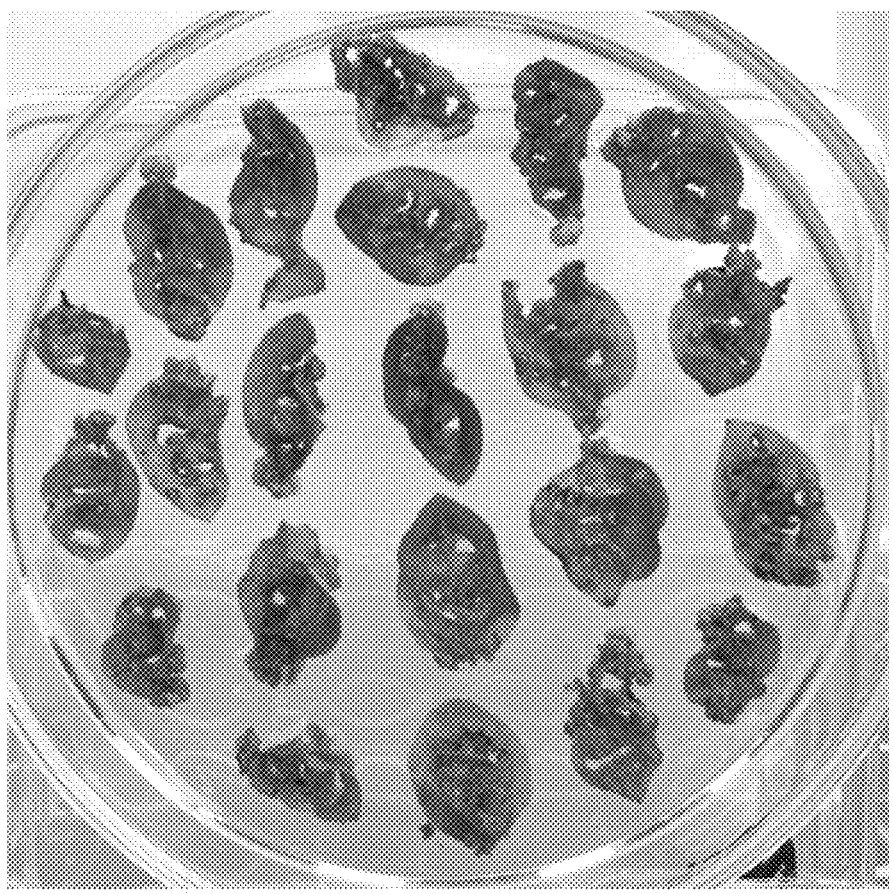
FIG. 5 is a photo of the callus induction and differentiation of Duke leaf.

Adopting the same operation methods and parameters as those in Example 1, and use #8 callus induction medium to conduct callus culture to the blueberry leaves of the Duke variety, wherein see FIG. 5 for the growth condition of one bottle after light culture of step (4).

Using stereomicroscope to observe the blueberry leaf with callus cultured by #8 callus induction medium, the magnification was 6.3 times, observing the callus and buds. See FIG. 6 for the photos of some views after light culture in step (4).

It can be seen from FIG. 5 that the callus induced by the leaf is light yellow or white, and it is visible to the naked eye that there has green dotted protrusions, the dotted protrusions are the differentiated blueberrybud primordium, the state and growth condition of bud primordium can be more clearly observed by stereomicroscope.

Figure 6:
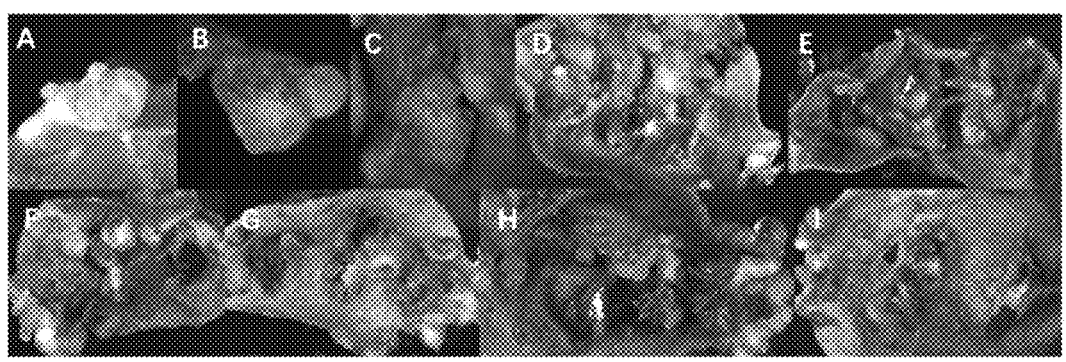
FIG. 6 is a photo of the callus induced from Duke leaf and the buds differentiated there from under the stereomicroscope.

The process that the callus differentiates into the bud (A-I) can be clearly seen from FIG. 6, they are respectively the emergence of bud primordium(A), the growth of bud primordium (B-D), the appearance of the bud (E), and the bud visible to the naked eyes (F-I), cut the buds in I, each can grow into a complete blueberry tissue culture seedling.

The #8 callus induction medium has similar callus induction effect on the blueberries of the Duke variety.

EXAMPLE 3

Influence of Leave and Medium Contact Surface to Callus Culture

The condition of using #8 callus induction medium in Example 1 is numbered as #1 in table 6; changing the front leaves surface (i.e., adaxial surface) in step (2) of Example 1 to the reverse leaves surface (i.e., abaxial surface) upwardly, other steps are the same as those of Example 1, which is numbered as #2 in table 6.

Observing the callus induction condition and growth, callus time, the state of callus, the color of callus, callus induction rate (only calculating living leaves) and callus differentiation rate of the explant (i.e., leaf tissue). See table 6 for concrete conditions.

As can be seen, as compared with the reverse leaves surface (i.e., abaxial surface) upwardly, the callus induction rate of the front leaves surface (i.e., adaxial surface) upwardly is slightly higher, and the callus differentiation rate is higher dramatically.

TABLE 6

Influence of leaf and medium contact surface to callus culture

| Serial number | Treatment mode | Time of callus | State of callus | Color of callus | Callus induction rate (only calculating living leaves) | Callus differentiation rate |
|---|---|---|---|---|---|---|
| 1 | Front leaves surface (i.e., adaxial surface) upwardly particles are less | 5-9 d | Compact, present small globular the surface small | White or light yellow | 97% | 71% |
| 2 | Reverse leaves surface (i.e., abaxial surface) upwardly, | 5-9 d | Compact, the surface small particles are more | White | 94% | 10% |

As can be known from technical common knowledge, the present invention can be achieved by other embodiments without separating the spiritual essence or essential features thereof. Therefore, in all aspects, all of the above disclosed embodiments are illustrated by examples, but not the only ones. All alterations in the scope of the present invention or equivalent to the scope of the present invention are included in the present invention.

What is claimed is:

1. A blueberry tissue expansion propagation method, comprising:
    inoculating cut, sterile blueberry leaf into a callus induction medium such that an abaxial surface of the cut, sterile blueberry leaf is adjacent to the callus induction medium, the callus induction medium consisting of
        woody plant medium (WPM), 4-8 g/L agar, 20-30 g/L sucrose, 2.0-4.0 mg/L forchlorfenuron (CPPU) and 0.1-0.4 mg/L 2-isopentenyladenine (2-ip),
        wherein the WPM consists of 400 mg/L Ammonium Nitrate, 370 mg/L Magnesium Sulfate Heptahydrate, 278 mg/L Calcium Nitrate Tetrahydrate, 200 mg/L Potassium Nitrate, 170 mg/L Potassium Dihydrogen Phosphate, 8.6 mg/L Zinc Sulfate Heptahydrate, 22.4 mg/L Manganese Sulfate Monohydrate, 0.25 mg/L Sodium Molybdate Dihydrate, 0.25 mg/L Copper Sulfate Pentahydrate, 73.4 mg/L Sodium Iron Ethylene Diamine Tetracetate, 100 mg/L Inositol, 2 mg/L Glycine, 0.5 mg/L Thiamine Hydrochloride, 0.5 mg/L Niacin and 0.1 mg/L Pyridoxine Hydrochloride,
    the callus induction medium having a pH in a range of 5.0-5.5;
    conducting an induction culture with the cut, sterile blueberry leaf in the callus induction medium for 12-22 days to form blueberry callus, during which the induction culture is maintained in a dark environment at a temperature of 22-26° C.;
    inoculating callus lumps of the blueberry callus into a bud growth medium consisting of
        the WPM, 4-8 g/L agar, 20-30 g/L sucrose, 1.0 mg/L CPPU and 0.4-0.6 mg/L 2-ip, with a pH falling in a range of 5.0-5.5, conducting a bud growth culture with the inoculated callus lumps to form a blueberry plant growing adventitious buds;

inoculating the blueberry plant growing adventitious buds into a rooting medium and conducting a rooting culture with the inoculated blueberry plant growing adventitious buds to form a blueberry plant growing adventitious buds and roots, the rooting medium consisting of 1/2 Murashige and Skoog (MS) medium, 5-9 g/L agar, 15-25 g/L sucrose and 2.0-3.0 mg/L naphthyl acetic acid (NAA), the rooting medium having a pH in a range of 5.0-5.5, wherein the 1/2 MS medium consists of 950 mg/L Potassium Nitrate, 166.1 mg/L Calcium Chloride, 825 mg/L Ammonium Nitrate, 90.35 mg/L Magnesium Sulfate, 85 mg/L Potassium Dihydrogen Phosphate, 0.025 mg/L Copper Sulphate, 6.2 mg/L Boric Acid, 16.9 mg/L Manganese Sulfate, 0.25 mg/L Sodium Molybdate, 8.6 mg/L Zinc Sulfate, 0.025 mg/L Cobalt Chloride, 0.83 mg/L Potassium Iodide, 27.8 mg/L $FeSO_4 \cdot 7H_2O$, 37.26 mg/L $Na_2$-$EDTA \cdot 2H_2O$, 2.0 mg/L Glycine, 100 mg/L Inositol, 0.50 mg/L Niacin, 0.1 mg/L Thiamine Hydrochloride, and 0.5 mg/L Pyridoxine Hydrochloride.

2. The tissue expansion propagation method of claim 1, wherein the variety of the blueberry is selected from the group consisting of JE, Duke, Bluecrop, and Sweetheart.

3. The tissue expansion propagation method of claim 1, wherein in the bud growth medium, the concentration of CPPU is 1.0 mg/L and the concentration of 2-ip is 0.4 mg/L; or in the rooting medium, the concentration of NAA is 2.0 mg/L.

4. The tissue expansion propagation method of claim 1, wherein the bud growth culture is conducted for 12-22 days, maintained at a temperature of 22-26° C., and lit 14-18 hours a day at a light intensity in a range of 1500-3000 lx; or the rooting culture is conducted for 15-35 days, maintained at a temperature of 22-26° C., and lit 14-18 hours a day at a light intensity in a range of 1500-3000 lx.

5. The tissue expansion propagation method of claim 1, further comprising:

inoculating the blueberry callus into a callus subculture medium consisting of WPM, 4-8 g/L agar, 20-30 g/L sucrose and 0.5-3.0 mg/L CPPD, the WPM consisting of 400 mg/L Ammonium Nitrate, 370 mg/L Magnesium Sulfate Heptahydrate, 278 mg/L Calcium Nitrate Tetrahydrate, 200 mg/L Potassium Nitrate, 170 mg/L Potassium Dihydrogen Phosphate, 8.6 mg/L Zinc Sulfate Heptahydrate, 22.4 mg/L Manganese Sulfate Monohydrate, 0.25 mg/L Sodium Molybdate Dihydrate, 0.25 mg/L Copper Sulfate Pentahydrate, 73.4 mg/L Sodium Iron Ethylene Diamine Tetracetate, 100 mg/L Inositol, 2 mg/L Glycine, 0.5 mg/L Thiamine Hydrochloride, 0.5 mg/L Niacin and 0.1 mg/L Pyridoxine Hydrochloride, the pH of the callus subculture medium falling in a range of 5.0-5.5; and conducting a callus subculture for 20-30 days, during which the blueberry callus inoculated in the callus subculture medium is maintained in a dark environment at a temperature between 22-26° C.

6. The tissue expansion propagation method of claim 1, further comprising:

hardening and then transplanting the blueberry plant growing adventitious buds and roots to obtain blueberry cultivated plant;

wherein said hardening comprises maintaining the inside of a culture bottle containing the blueberry plant growing adventitious buds and roots at 65-75% humidity for 0.5-1.5 days, then maintaining the inside of the culture bottle at 55-65% humidity for 5-9 days under ventilated conditions; and wherein, during said hardening, the blueberry plant growing adventitious buds and roots is lit for 14-18 hours a day at a light intensity in a range of 1500-3000 lx.

* * * * *